United States Patent [19]

Dring et al.

[11] Patent Number: 5,000,939
[45] Date of Patent: Mar. 19, 1991

[54] DENTIFRICE CONTAINING STABILIZED ENZYME

[75] Inventors: Timothy Dring, Wharton; Diane McPherson, Whitehouse Station, both of N.J.; Debbie Moy, New York, N.Y.

[73] Assignee: Colgate-Palmolive Company, Piscataway, N.J.

[21] Appl. No.: 798,136

[22] Filed: Nov. 14, 1985

Related U.S. Application Data

[63] Continuation of Ser. No. 619,879, Jun. 12, 1984, abandoned.

[51] Int. Cl.$^5$ .......................... A61K 9/68; A61K 7/28
[52] U.S. Cl. ........................................ 424/48; 424/50
[58] Field of Search ..................................... 424/50, 48

[56] References Cited

U.S. PATENT DOCUMENTS

| | | | |
|---|---|---|---|
| 3,957,967 | 5/1976 | L'Orange | 424/54 |
| 3,981,989 | 9/1976 | Suganuma et al. | 424/50 |
| 4,391,798 | 7/1983 | Tavss et al. | 424/52 |
| 4,466,954 | 8/1984 | Ichikawa et al. | 424/49 |

FOREIGN PATENT DOCUMENTS 1270200  4/1972  United Kingdom ............... 424/50

*Primary Examiner*—Jacqueline Stone
*Attorney, Agent, or Firm*—Michael J. McGreal; Robert C. Sullivan; Murray M. Grill

[57] ABSTRACT

Stable oral compositions containing the enzyme dextranase, a mixed surfactant system of anionic and amphoteric surfactants, and a cationically modified hydrolyzed collagen stabilizer, which stabilizer the dextranase in the presence of the anionic surfactant without substantially reducing its foaming and cleansing properties.

15 Claims, No Drawings

DENTIFRICE CONTAINING STABILIZED ENZYME

This application is a continuation of application Ser. No. 619,879, filed June 12, 1984, now abandoned.

BACKGROUND AND PRIOR ART

The present invention relates to novel dextranase-containing dentifrices which are enzymatically, physically and cosmetically stabilized in the presence of anionic surfactants by the addition of a dual anionic and amphoteric betaine surfactant system and a cationically modified hydrolyzed collagen protein stabilizer, to provide formula stability and retention of enzyme activity over time.

The prior art is replete with information relating to the effectiveness of dextranase against dental plaque, its dispersion and removal, as shown in an article by Bowen in the *British Dental Journal*, vol. 24 number 8, pp. 347–349, (Apr. 16, 1968); an article by Fitzgerald et al, in *JADA*, vol. 76, pp. 301–304, (February 1968); and an article by Duany et al, in *Journal of Preventive Dentistry*, vol. 2, No. 2, pp. 23–27, (March–April 1975). The dextranase enzymes also reduce the formation of dental caries and periodontal disease when applied topically. These enzymes degrade or break down the dextrans synthesized in the plaque from sucrose by *strep. mutans*. The dextrans serve as a glue for the cohesion of the plaque.

Accordingly, dextranase has been incorporated in conventional oral hygiene products such as toothpastes, rinses and chewing gum containing surface active cleansing and foaming agents, as shown in Japanese Patent Public Disclosure No. 56834/1973, and in British Patent No. 1,319,423 containing an anionic surfactant. These surfactants, especially anionic surfactants, tend to deactivate the enzymes such as dextranase, with rapid loss of enzyme activity in the absence of stabilization. Thus, it is difficult to make a stable and foaming dentifrice with dextranase. Accordingly, a number of stabilizers have been incorporated in dentifrice compositions containing dextranase. For example, U.S. Pat. No. 3,991,177 teaches the use of manganous and calcium ions to stabilize dextranases in the dentifrices in the presence of anionic surfactant such as sodium N-lauroyl sarcosinate. U.S. Pat. No. 3,981,989 discloses gelatin or peptone as the stabilizing agents for dextranases in the presence of sodium lauryl sulfate. U.S. Pat. No. 4,140,758 teaches the use of a metal ion selected from the group consisting of manganese, calcium, magnesium and mixtures thereof as a stabilizer/activator for dextranase. Japanese Patent No. 013318 by Lion, dated 2/6/1980, utilizes eugenol and 1-menthol as dextranase stabilizers in the presence of anionic surfactants. Japanese Patent No. 010350 by Lion Corp., dated 1/27/81, utilizes a mixture of dextranase and omega-amino acids in oral compositions to prevent bacterial plaque formation. French Patent Application No. 82/05799 discloses an oral composition comprising a mixture of dextranase and α-1,3 glucanase. U. K. Patent Application No. 2,061,727A utilizes aluminas and hydrated aluminas as the abrasive, in order to stabilize the dextranase in the dentifrice composition.

U.S. Pat. No. 3,562,385 discloses dental antiplaque and anticalculus compositions containing a mixture of a bis-biguanido compound, dextranase and sodium hexametaphosphate. U.S. Pat. No. 3,622,661 discloses oral preparations containing dextranase and the specific binder Irish moss or gum tragacanth to prevent separation upon standing. Oral antiplaque and/or anticalculus compositions containing dextranase are also disclosed in U.S. Pat. Nos. 3,630,924; 3,686,393; and 3,751,561. Oral compositions containing dextranase in combination with other enzymes are disclosed in U.S. Pat. No. 4,335,101. Dextranase has been modified by molecular alteration by the use of a phosphoprotein carrier and a reacting agent such as ethylchloroformate, in order to provide longer periods of activity in the oral cavity, as disclosed in U.S. Pat. No. 4,138,476.

Toothpastes having cosmetic and enzymatic stability containing a neutral protease of *B. subtilis*, stabilized by a partially hydrolyzed protein is disclosed in U.S. Pat. No. 4,058,596. The addition of a Group IIA metal ion to the neutral protease and hydrolyzed protein combination provides additional stability as disclosed in U.S. Pat. No. 4,058,595.

Although the problem of stabilizing dextranase in the presence of anionic surfactants is well known in the prior art, and has been solved by the addition of a variety of stabilizing agents as aforecited, there is no disclosure of the use of a dual surfactant system of anionic surfactants and amphoteric betaine and a cationically modified hydrolyzed collagen protein stabilizer, such as a quaternized hydrolyzed protein (Crotein Q).

SUMMARY OF THE INVENTION

It has been unexpectedly found that the addition of a quaternized hydrolyzed collagen protein stabilizer to a dentifrice comprising a dextranase enzyme, and a dual surfactant system of an anionic surfactant and an amphoteric betaine, provides better shelf-life stability for the enzyme than gelatin and other prior art enzyme stabilizers, without adversely affecting the foaming power or detergency of the anionic surfactant.

Accordingly, a primary object of present invention is to provide a stable dentifrice containing a dual surfactant system of an anionic surfactant and an amphoteric betaine, a dextranase enzyme and a quaternized hydrolyzed collagen protein stabilizer.

Another object of present invention is to provide a foaming and stable dextranase-containing dentifrice in the presence of anionic and amphoteric surfactants.

Still another object of present invention is to provide a physically and cosmetically stable dextranase-containing dentifrice with retention of enzyme activity over time.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the present invention, as embodied and broadly described herein, the stable dentifrice of this invention comprises dextranase, a dual surfactant system of an anionic surfactant and an amphoteric betaine, in the molar ratio of 1:1 to 1:2 and preferably 1.2:1 respectively, and a cationically modified hydrolyzed collagen protein stabilizer, typically, a quaternary derivative of hydrolyzed protein, in a dental vehicle.

In accordance with certain of its further aspects, the present invention relates to a stable oral composition, which may be in the form of a powder, paste, cream, liquid or chewing gum, comprising a dual surfactant system of an anionic surfactant and an amphoteric betaine in the molar ratio of 1.2:1 respectively, a dextranase in an amount to provide 5,000 to 55,000 units/g of initial enzyme activity, and a quaternized hydrolyzed collagen protein stabilizer in a weight ratio of 1:1 to 1:2 of anionic surfactant to the cationically modified hydrolyzed protein stabilizer.

Dextranase enzymes are produced from a variety of sources all of which are useful in the present invention. Dextranase enzymes are commonly produced by growing *Penicillium funiculosium* or other fungal sources in a dextran-containing medium. The dextran is commonly a commercial grade obtained from *Leuconostoc mesenterioides*. This commercial grade of dextran contains about 95-percent α-1,6-glucoside linkages and about 5 percent α-1,3-glucoside linkages. The Penicillium organism produces the dextranase which particularly hydrolyzes the 1,6-linkages.

Dextranase may also be prepared in accordance with procedures which are described in the art. These include the procedure described by Bowen, "British Dental Journal," Vol. 124, No. 8, dated Apr. 16, 1968, pages 343-349. A further procedure is described in U.S. Pat. No. 2,742,399 to Tsuchiya et al. (Note also Tsuchiya et al, "Journal of Bacteriology," Vol. 64, page 513).

In the procedure of Bowen, dextran may be prepared from noncariogenic streptococcal strains such as ATCC 10558, 903-1600, IIA2+3, or Leuconostoc mesenterioides and purified according to the method described by Wood et al, "Archives of Oral Biology," Vol. 11, 1066, pages 1039 ct seq., except that *L. mesenterioides* is grown at 25° C.

Dextranase may be prepared by inoculating *Penicillium funicolosum* into flasks containing 250 ml of a medium containing 0.5% yeast extract and 1% dextran. The flasks are incubated at 30° C. on a shaking incubator for 4 days. The culture is then centrifuged at 3,000 g for 20 minutes and filtered through Whatman 42 filter paper. Dialysis in 16 mm "Visking" tubing against deionized water and concentrating fifty fold by dialysis against polyethylene glycol (molecular weight 20,000) follows. The dextranase produced in accordance with this procedure has a molecular weight of about 200,000 to 275,000. If desired, the dextranase may be further purified by fractionation with ammonium sulfate.

Additional procedures for preparing dextranase include that described in U.S. Pat. No. 2,742,399 to Tsuchiya et al.

Dextranases of bacterial origin are also useful in the present compositions. Bacterial-origin dextranase may be prepared in the general manner in which enzymes are derived from bacteria. However, the preferred source of dextranase for the purposes of this invention is a mutant of Bacillus coagulans, NRRL B-3977 (Beckman dextranase catalogue #680000). Bacterial-origin dextranase may be obtained by the addition of α-1,3-dextran or a mixture of α-1,6-, α-1,3-, and α-1,4-dextrans.

The bacterial strain may be innoculated into a shaker flask or fermentator for a period of 1 to 5 days at 25°-40° C. The sterile growth medias can consist of the aforementioned dextran or mutan combined with a mixture of carbohydrate (starch, glucose, sucrose, cellulose), nitrogenous compounds (protein digest, gelatin, casein, ammonium salts), growth stimulators, (yeast extract, corn steep liquor, distiller's solubles), or minerals. Preservatives may be added and the enzyme decanted, filtered, or centrifuged to precipitate the cells (intracellular dextranase). The extracellular dextranase can be precipitated with ammonium sulfate, acetone, sodium sulfate, or a similar salt. The intracellular dextranases are autolyzed and extracted. Following the salt fractionation step, the enzyme can be further purified by a variety of column (DEAE, Sephodex, ECTEOLA, hydroxyapatite) chromatography methods and frozen or stabilized by the addition of protein, dextran, salt, etc. (The purification steps are usually conducted at refrigerated temperatures.)

The amount of dextranase employed in the oral compositions of the invention is at least such amount as is effective in promoting oral hygiene. This amount is dependent upon the activity of the dextranase which may typically range from 5,000-55,000 units/g and therefore upon the mode of its preparation. A typically prepared dextranase enzyme material has an activity of about 10,000 units/g. Enzyme activity units are defined as the microgram (mg) of product formed (glucose) per minute per gram of dentifrice referred to a Glucose standard curve as set forth in the Journal of Bacteriology, Vol. 64(4), pages 513-514 (1952), which is more fully discussed hereinafter.

While smaller amounts of dextranase may be used, dextranase having an activity of about 5,000-55,000 units/g may be present in amounts of about 0.5-4% by weight of the oral composition.

The dentifrice of this invention preferably contains 5,000-55,000 units/g dentifrice of initial enzyme activity and exhibits physical and cosmetic stability and the retention of enzyme activity over time (at least 75% enzyme activity after 12 weeks of aging at 100° F.).

It is essential that present dextranase-containing dentifrice comprise a dual surfactant system of an anionic surfactant and an amphoteric surfactant selected from the class consisting of betaines and sulfobetaines, in a molar ratio of about 1:1 to 1:2 respectively.

An important consideration in the surfactant system is the molar ratio of sodium lauryl sulfate (SLS) to betaine, with the optimum being approximately 1.2 to 1 respectively. It is believed that the desirability of this ratio is due to the optimum establishment of a mixed micelle system helping to moderate the denaturing effect of the sodium lauryl sulfate. Increasing the betaine to an amount resulting in an SLS to betaine ratio of 1:2 or more produces a stable dentifrice with unsatisfactory taste characteristics. This surfactant system generates a stable foam and assists in achieving thorough and complete dispersion of the composition throughout the oral cavity. J. Garcia Dominguez, *International Journal of Cosmetic Science*, Volume 3, pp. 57-68 (1981), discloses that amphoteric betaine inhibits sodium lauryl sulfate from denaturing dextranase in an aqueous solution, by the formation of mixed micelles through ionic interaction with SLS. However, its use in a dentifrice together with the cationic protein stabilizer affords unexpected and unusual formula stability and the retention of enzyme activity upon aging.

The anionic surface active agents contain a sulfonate, sulfate, carboxylate or phosphate as the anionic water solubilizing group. Examples of suitable anionic detergents include the soaps, such as the water soluble salts of higher fatty acids or rosin acids, such as may be derived from fats, oils and waxes of animal, vegetable or marine origin, e.g., the sodium soaps of tallow, grease, coconut oil, tall oil and mixtures thereof; and the sulfated and sulfonated synthetic detergents, particularly those having about 8-26, and preferably about 12-22, carbon atoms to the molecule. Examples of suitable synthetic anionic detergents include the higher alkyl mononuclear aromatic sulfonates such as the higher alkyl benzene sulfonates containing from 8-16 carbon atoms in the alkyl group in a straight or branched chain, e.g., the sodium salts of decyl, undecyl, dodecyl (lauryl), tridecyl, tetradecyl, pentadecyl, or hexadecyl benzene sulfonate and the $C_8$-$C_{16}$ alkyl toluene, xylene and phenol sulfonates: $C_8$-$C_{16}$ alkyl naphthalene sulfonate, ammonium diamyl naphthalene sulfonate, and sodium dinonyl naphthalene sulfonate; sulfated aliphatic alcohols such as sodium lauryl and hexadecyl sulfates, triethanolamine lauryl sulfate, and sodium oleyl sulfate; sulfated alcohol ethers, such as lauryl, tridecyl, or tetradecyl sulfates including 1-5 ethylene oxide moieties; ammonium lauryl ether sulfate; sulfated and sulfonated fatty oils, acids or esters, such as the sodium salts of sulfonated castor oil and sulfated red oil; sulfated hydroxyamides such as sulfated hydroxyethyl lauramide; sodium slat of lauryl sulfoacetate; sodium salt of dioctyl sulfosuccinate, the sodium salt of oleyl methyl tauride, and sodium N-lauryl sarcosinate.

Also included within the ambit of the invention are the sulfuric acid esters of polyhydric alcohols incompletely esterified with higher fatty acids, e.g., coconut oil monoglyceride monosulfate, tallow diglyceride monosulfate; and the hydroxy sulfonated higher fatty acid esters such as the higher fatty acid esters of low molecular weight alkylol sulfonic acids, e.g., oleic acid ester of isethionic acid.

The anionic surfactants most often used are the ammonium, mono-, di- and triethanolamine, and alkali metal (sodium and potassium) salts of the higher alkyl benzene sulfonates, the higher alkyl sulfates, the higher fatty acid monoglyceride sulfates and the sulfated ethoxylated alcohols, ammonium lauryl ether sulfate, sodium N-lauroyl sarcosinate, dioctyl sodium sulfosuccinate, and mixtures thereof.

It is preferred to use the anionic surfactant in an amount of about 0.5 to 5% by weight of the carrier.

The amphoteric surfactant, the other essential member of the dual surfactant system, has both anionic and cationic groups, is ionically balanced, and its isoelectric point is at a pH of about 7 and includes the betaines and sulfobetaines. The betaines are a class of amphoteric surfactants which include alkyl betaines, alkylamido betaines and alkylamino betaines having the general formula:

$$R_1 - \underset{\underset{R_3}{|}}{\overset{\overset{R_2}{|}}{N^+}} - R_4 - COO^-$$

wherein $R_1$ is an alkyl group having 10 to about 20 carbon atoms, preferably 12 to 16 carbon atoms or the amido radical:

$$R - \underset{}{\overset{O}{\overset{\|}{C}}} - \underset{}{\overset{H}{\overset{|}{N}}} - (CH_2)_a -$$

or an amino radical:

$$R - NH - (CH_2)_a -$$

wherein R is an alkyl group having about 10 to 20 carbon atoms and a is the integer 1 to 3; $R_2$ and $R_3$ are each alkyl groups having 1 to 3 carbons and preferably 1 carbon; $R_4$ is an alkylene or hydroxyalkylene group having from 1 to 4 carbon atoms and, optionally, one hydroxyl group. Typical alkyldimethyl betaines include decyl betaine or 2-(N-decyl-N,N-dimethylammonio) acetate, coco betaine or 2-(N-coco-N,N-dimethylammonio) acetate, myristyl betaine, palmityl betaine, lauryl betaine, cetyl betaine, stearyl betaine, etc. The amidobetaines similarly include cocoamidoethyl betaine, cocoamidopropyl betaine, lauramidopropyl betaine and the like.

The sulfobetaines, which are similar in structure to the betaines, have sulfonate groups in place of the carboxylate groups, as represented by the general formula:

$$R_1 - \underset{\underset{R_3}{|}}{\overset{\overset{R_2}{|}}{N^+}} - R_4 - SO_3^-$$

wherein $R_1$, $R_2$, $R_3$ and $R_4$ have the same meanings as above, and include alkylsulfobetaines, alkylamidosulfobetaines and alkylaminosulfobetaines.

The molar ratio of anionic to amphoteric surfactant of 1:1, 1.2:1 and up to 1:2, afford good dextranase stability in the presence of a polycationic stabilizer such as Crotein Q. It is preferred to use the amphoteric surface active agent in an amount of about 2-6% by weight of the carrier.

The inactivation of the dextranase due to the presence of the anionic surfactant in the dentifrice makes it additionally necessary to add about 1-5% by weight of a cationic stabilizer, having multiple positive charges, to also interact with the anionic surfactant sodium lauryl sulfate (SLS), thereby reducing its ability to interact with the enzyme dextranase. The stabilizer is a cationically modified hydrolyzed collagen protein. More specifically, said stabilizer is a quaternary derivative of hydrolyzed collagen protein. The ratio of cationic stabilizer:anionic surfactant is within the weight range of about 1:1 to 2:1 respectively in order to assist in binding the anionic surfactant and prevent its interaction with dextranase.

The quaternary derivative of hydrolyzed collagen protein is a product of Croda Inc. of New York, known as Crotein Q, having a minimum pI of 9.5-10.5, is an off-white free flowing powder and its adopted name is steartrimonium hydrolyzed animal protein. The free amino groups in the protein molecule react with the quaternary ammonium reactant to form the quaternized derivative which has multiple positive charges. At pH's below 5.5, Crotein Q will exhibit a double positive charge, due to protonation of NH groups in the protein chain, as shown diagrammatically in the Crodata circular 7778, page 2.

Stability studies conducted on dextranase enzymes have shown that the enzyme inactivating effects of anionic surfactants such as sodium lauryl sulfate can be substantially decreased in the presence of an amphoteric surfactant such as betaine and a polycationic stabilizer, such as Crotein Q. Although the exact mechanism by which this combination of stabilizers effect this function is not known, it is hypothesized that both the Crotein Q and the betaine preferentially prevent the reaction of the enzyme with the anionic surfactants. The preferential interaction of the stabilizers with the anionic surfactant(s) prevents the anionic surfactant-inactivation of the dextranase.

The stability of the dextranase-containing dentifrice is measured by the retention of enzyme activity over a protracted period of time as shown in Table I, wherein comparative samples of said dentifrice containing a dual surfactant system of anionic and amphoteric surfactant are used. The manual method of Tsuchiya et al, *Journal of Bacteriology*, Vol. 64 (4) pp. 513-514, (1952), is used to determine retention of enzyme activity and may be modified for the Technicon autoanalyzer, both using the colorimetric reagent dinitrosalicylic acid. Aged samples solubilized in water and buffer were incubated for 11.5 minutes with dextran substrate, the reaction stopped by boiling, the solution reacted with color reagent, and the absorbance read and compared to a glucose standard curve to determine the percent enzyme activity remaining. Despite inconsistencies in the enzyme activities detected for aged dentifrice samples which showed increasing activity with age, trends evidenced a gradual loss in dentrifice enzyme activity by the end of 12 weeks of aging at 100° F. In the case of some of the better formulations this was spot-checked and verified by manual analysis to be a loss of up to 30% at 12 weeks using the method described above.

Examples 1-3 inclusive are more fully defined hereinafter.

Examples 4-10 inclusive represent other stable dual surfactant dentifrice formulae utilizing conventional humectants, thickening agents, flavors and the like, in conventional amounts as set forth in this specification.

TABLE I

SLS/Betaine/Dextranase Formulations and Aging Data

| Ex. | Ingredients | Initial Enzyme Activity | % of Initial Enzyme Activity | | | |
|---|---|---|---|---|---|---|
| | | | 3 wks | 6 wks | 9 wks | 12 wks |
| 1 | 3.6% Dextranase (0.83 mg protein/ml), 2% Crotein Q, 1.8% SLS, 5% Betaine, Silica | 53,130 | 104 | 98 | 103 | 99 |
| 2 | 3.6% Dextranase (0.83 mg protein/ml), 2% Crotein Q, 1.8% SLS, 5% Betaine, Alumina | 49,392 | 100 | 98 | 87 | 79 |
| 3 | 0.65% Dextranase (0.83 mg protein/ml), 1% Crotein Q, 1.2% SLS, Alumina | 5,340 | 0 | 0 | 0 | 0 |
| 4 | Alumina, 2% Crotein Q, 1.2% SLS, 4% Betaine[1], 0.55% Dextranase | 4,570 | 110 | 101 | 95 | 83 |
| 5 | Silica, 2% Crotein Q, 1.2% SLS, 4% Betaine, 1% Amide, 2.1% Dextranase | 18,600 | 84 | 71 | 67 | 81 |
| 6 | Alumina, 2% Crotein Q, 1.2% SLS, 4% Betaine, 1.8% Dextranase | 13,800 | 99 | 88 | 107 | 107 |
| 7 | Alumina, 2% Crotein Q, 0.3% SLS, 0.9% ALES[2], 4% Betaine, 1.8% Dextranase | 13,400 | 91 | 95 | 116 | 113 |
| 8 | Alumina, 2% Crotein Q, 0.3% SLS, 0.9% ALES, 4% Betaine, 3.6% Dextranase | 27,000 | 103 | 99 | 123 | 121 |
| 9 | Silica, 2% Crotein Q, 0.3% SLS, 0.9% ALES, 4% Betaine, 3.6% Dextranase | 28,300 | 102 | 99 | 120 | 119 |
| 10 | Alumina, 3% Crotein Q, 1.2% SLS, 5% Betaine, 3.6% Dextranase | 23,200 | 104 | 141 | 139 | 148 |

[1] Sulfated amido-betaine
[2] Ammonium laurylether sulfate (60% active)

Samples were aged at 100° F. Activities determined by colorimetric spectrophotometry using 3,5 dinitrosalicylic acid.
Calculations:
SLS (94% active, F.W. 288.38) 18 grams × 0.94 = 16.9 g = 0.0587 moles
Betaine (27% active, F.W. 283) 50 grams × 0.27 = 13.5 g = 0.0477 moles
ALES (60% active, F.W. 432)
Molar ratio SLS: Betaine = 0.06:0.05 = 1.2:1

A molar ratio of about 1:1 or 1.2:1 between anionic and amphoteric is best, perhaps due to the formation of a mixed micelle solution of anionic/amphoteric whereby the SLS is prevented from denaturing the dextranase enzyme. Deletion of the betaine causes the dentifrice to rapidly lose its enzyme activity with aging as shown below:

| Ingredients | Molar ratio | Enzyme Activity Recovery @ 12 weeks |
|---|---|---|
| 1.2% SLS, 4% betaine | 1.2:1 | 110% |
| 1.5% SLS, no betaine | — | 0% |

The interactions of both stabilizers with the anionic surfactant to prevent its interaction with dextranase does not substantially reduce the foaming ability of the anionic agent. The foaming properties of the surfactants were measured according to standard foam height procedure. This analysis was conducted at 37° C. in both distilled and hard water (105 ppm $CaCl_2$, and 70 ppm $MgCl_2$). Solutions were prepared to contain singularly or combinations of 0.1% SLS, or 1% betaine and/or 0.2% Crotein Q. Foam volume was measured in ml after 30 inversions of the graduate cylinder. The following graph shows the relative foam volumes in distilled water and hard water.

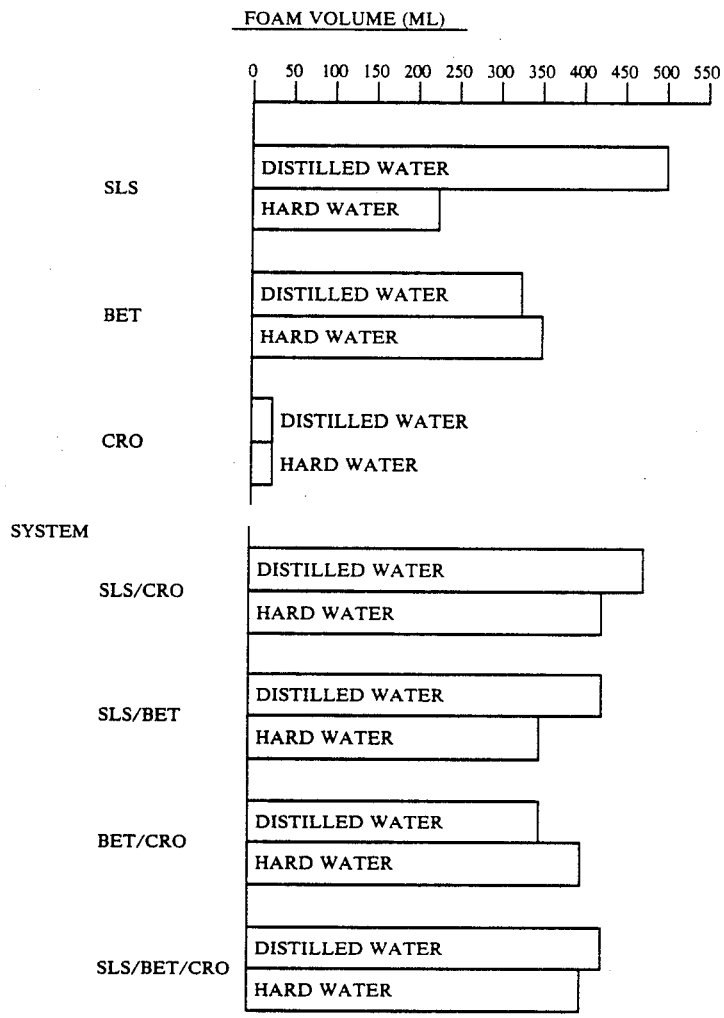

This data shows that in distilled water, SLS produces the largest volume of foam. Those combinations containing SLS and Crotein foamed better than the combination of SLS and betaine, Crotein and betaine, and betaine alone. It is also noted that Crotein does not readily reduce SLS foaming although betaine does. In the hard water, foaming of SLS is drastically reduced, whereas foaming by betaine is unchanged. In hard water, foaming by SLS is greatly enhanced by the stabilizer Crotein. Overall, these results indicate that the system providing optimal enzyme stabilization, SLS+Crotein+betaine exhibits good foaming characteristics regardless of the water hardness. This point is important since the divalent cation concentration in the oral cavity is quite high.

Accelerated aging studies further show that enzymatically, physically and cosmetically stable dentifrices containing approximately 5,000 units of dextranase per gram of dentifrice exhibit good foaming in the presence of betaine, and anionic surfactants and the cationic stabilizer as shown in Table II.

TABLE II

| Sample | Ingredients | % of initial Exzyme Activity | Aged at 100° F. | *Height of Foam (ml) |
| --- | --- | --- | --- | --- |
| 1 | Alumina - 1.2% Betaine, 1.2% SLS, 2% Crotein Q | 95 | 9 wks | 54 |
| 2 | Alumina - 0.9% Betaine, 0.8% SLS, 1% Crotein Q | 96 | 9 wks | 34 |
| 3 | Alumina - 1.2% Betaine, 0.6% SLS, 1% Crotein Q | 98 | 9 wks | 30 |
| 4 | Silica - 1.2% Betaine, 0.6% SLS, 2% Crotein Q | 104 | 6 wks | 32 |
| 5 | Alumina - 1.2% Betaine, 0.6% SLS, - | 83 | 9 wks | 35 |
| 6 | Alumina - 1.2% Betaine, 0.5% SLS, - | 89 | 9 wks | 32 |

*The height of foam was measured after shaking 1 gram of dentifrice in 10 ml of 175 PPM hard water (90° F.) for 15 sec.

Toothpastes and toothpowders conventionally contain a substantially water insoluble polishing agent or abrasive which is compatible with the formulation. Preferred compatible materials which do not adversely affect the dentifrice composition include dicalcium phosphate dihydrate, silica and hydrated alumina. The polishing agent may be the sole carrier material as in a toothpowder, and is present in an amount up to about 80% of the carrier and generally about 30–75% of the carrier.

In toothpaste formulations the liquids and solids should necessarily be proportioned to form a creamy mass having the desired consistency which is extrudable from a pressurized container or a collapsible tube (for example, aluminum or lead). In general, the liquids in the toothpaste will comprise chiefly water, glycerin, aqueous solutions of sorbitol, propylene glycol, polyethylene glycol 400, etc., and suitable mixtures thereof. It is advantageous usually to use a mixture of both water and a humectant or binder such as glycerin or sorbitol. The total liquid content will generally be about 20–75% of the carrier. The amount of water is generally about 10–25% of the carrier. It is preferred to also use a gelling agent in toothpastes such as the natural and synthetic gums and gum-like materials such as Irish moss, gum tragacanth, carboxymethyl cellulose, Viscarin GMC, Iota carrageenan, starch, sodium alginate, and the like, usually in an amount up to about 10%, and preferably about 0.2–5%, of the carrier.

The carrier suitably may contain a fluorine-containing compound having a beneficial effect on the care and hygiene of the oral cavity, for example, diminution of enamel solubility in acid and protection of the teeth against decay. Examples thereof include stannous fluoride, potassium stannous fluoride, sodium hexafluorostannate, stannous chlorofluoride, sodium fluorozirconate, and sodium monofluorophosphate. These materials, which dissociate or release fluorine containing ions in water, suitably may be present in the carrier in an effective but nontoxic amount, usually within the range of about 0.1–5% by weight.

Various other materials may also be incorporated into the carrier. Examples thereof are coloring or whitening agents (for example, titanium dioxide), preservatives (for example, sodium benzoate), silicones, chlorophyll compounds, ammoniated materials such as urea, diammonium phosphate, and mixtures thereof, alcohol, menthol, and other constituents. These adjuvants are incorporated into the instant compositions in amounts which do not substantially adversely affect the properties and characteristics and are suitably selected and used in proper amount depending upon the particular type of preparations involved.

Flavoring or sweetening materials of the type commonly employed in dentifrices may be included in the carrier. Such materials, if present, aid in modifying the particular tastes of the flavor in the manner desired. Examples of such additional materials include the flavoring oils, for example, oils of spearmint, peppermint, wintergreen, sassafras, clove, sage, eucalyptus, marjoram, cinnamon, lemon, and orange, as well as methylsalicylate. Suitable sweetening agents include sucrose, lactose, maltose, sorbitol, sodium cyclamate, and saccharin. Suitably, the flavor and sweetening agent may together comprise about 0.01–2% of the carrier.

The dentifrice may be prepared by suitably mixing the ingredients. For instance in making a toothpaste, a gelling agent such as sodium carboxymethyl cellulose or Iota carrageenan and a preservative such as sodium benzoate, if employed, is dispersed in a humectant such as glycerin. Water may also be present. Additional humectant and water may then be mixed with the dispersion and a homogeneous paste, gel or cream is formed. Dental abrasive agent, surface active agents and flavor are then added. The toothpaste is then thoroughly deaerated (e.g., in vacuo) and tubed. The formulation may be deaerated during mixing or after mixing.

DETAILED DESCRIPTION OF THE INVENTION

The following examples are merely illustrative of the invention, but it is understood that the invention is not limited thereto. All amounts of various ingredients are by weight unless otherwise specified.

EXAMPLE 1

| Gel Toothpaste | |
|---|---|
| Ingredients | % |
| Glycerine | 25 |
| CMC[1] | 0.35 |
| Na Benzoate | 0.5 |
| Na Saccharin | 0.2 |
| Sodium Monofluorophosphate (MFP) | 0.76 |
| Sorbitol | 24.09 |
| Carbowax - PEG 600[2] | 3 |
| FDC Blue #1 @ 1% | 0.1 |
| Deionized water | 6.6 |
| Silica containing combined alumina[3] | 18 |
| Colloidal silica aerogel[4] | 8 |
| Sodium lauryl sulfate (SLS) | 1.8 |
| Betaine tego-S-1066[5] | 5 |
| Crotein Q | 2 |
| Flavor | 1 |
| Dextranase (20,000 units/g) | 3.6 |
| pH | 6.5 |
| Foam | 84 ml |

[1]Carboxymethyl cellulose
[2]Polyethylene glycol, mol. weight 600
[3]Zeo 49B, ex J. M. Huber
[4]Syloid 244
[5]A sulfated amphoteric surfactant manufactured by Goldschmidt Chemical Corp., Actives 27%

EXAMPLE 2

| Toothpaste | |
|---|---|
| Ingredients | % |
| Iota carrageenan | 0.9 |
| Glycerine | 22 |
| Na Benzoate | 0.5 |
| Na Saccharin | 0.2 |
| MFP | 0.76 |
| Deionized water | 12.24 |
| Hydrated alumina | 50 |
| SLS | 1.8 |
| Sulfated amidobetaine (1.5% active) | 5 |
| Crotein Q | 2 |
| Flavor | 1 |
| Dextranase (20,000 units/g) | 3.6 |
| pH | 7.41 |
| Foam | 83 ml |

EXAMPLE 3

| Toothpaste | |
|---|---|
| Ingredients | % |
| Iota carrageenan | 0.9 |
| Glycerin | 22 |
| Na Saccharin | 0.2 |
| Methyl Paraben | 0.1 |
| MFP | 0.76 |
| Crotein Q | 1 |
| Deionized water | 23.19 |
| Hydrated alumina | 50 |
| SLS | 1.2 |
| Dextranase (20,000 units/g) | 0.65 |

| Toothpaste | |
|---|---|
| Ingredients | % |
| pH | 8.08 |

The omission of the betaine reduces the enzyme stability of this composition to zero.

EXAMPLE 4

| Toothpaste | |
|---|---|
| Ingredients | % |
| Iota carrageenan | 0.9 |
| Glycerin | 22.0 |
| MFP | 0.76 |
| Na Benzoate | 0.5 |
| Na Saccharin | 0.2 |
| Hydrated alumina | 50 |
| SLS | 1.2 |
| Betaine | 4.0 |
| Crotein Q | 2 |
| Flavor | 1 |
| Dextranase (10,000 units/g) | 1.8 |
| Deionized water | 15.64 |
| pH | 7.44 |
| Foam | 58 ml |

EXAMPLE 5

| Toothpaste | |
|---|---|
| Ingredients | % |
| Iota carrageenan | 0.9 |
| Glycerin | 22 |
| Na Benzoate | 0.5 |
| No Saccharin | 0.2 |
| MFP | 0.76 |
| Hydrated alumina | 50 |
| Deionized water | 13.64 |
| SLS | 1.2 |
| Betaine tego-S 1066 | 5 |
| Crotein Q | 3 |
| Flavor | 1 |
| Dextranase (10,000 units/g) | 1.8 |
| pH | 7.17 |
| Foam | 71 ml |

EXAMPLE 6

| Toothpaste | |
|---|---|
| Ingredients | % |
| Iota carrageenan | 0.9 |
| Glycerin | 22 |
| Na Benzoate | 0.5 |
| No Saccharin | 0.2 |
| MFP | 0.76 |
| Hydrated alumina | 50 |
| Deionized water | 11.84 |
| SLS | 1.2 |
| Betaine | 5 |
| Crotein Q | 3 |
| Flavor | 1 |
| Dextranase (20,000 units/g) | 3.6 |
| pH | 7.28 |

| Toothpaste | |
|---|---|
| Ingredients | % |
| Foam | 60 ml |

EXAMPLE 7

| Mouthwash | |
|---|---|
| Ingredients | % |
| Ethanol (90%) | 5-10 |
| Glycerin | 10-20 |
| Sodium Saccharin | 0-5 |
| Sodium Benzoate | 0-5 |
| Betaine | 1-2 |
| Dextranase (5,000-20,000 units/ml) | 0.05-1 |
| Sodium Lauryl Sulfate (SLS) | 0.1-0.5 |
| Crotein Q | 0.5-3 |
| Flavoring | 0.22-0.5 |
| Water | Q.S. |

EXAMPLE 8

| Toothpowder | |
|---|---|
| Ingredients | % |
| Hydrated alumina | 70-80 |
| Glycerin | 10 |
| SLS | 0.1-0.5 |
| Betaine | 0.5-1.0 |
| Sodium Saccharin | 0.1 |
| Flavoring | 1.0 |
| Dextranase | 5,000-20,000 units/g |
| Crotein Q | 0.5-3 |
| Water | Q.S. |

EXAMPLE 9

| Chewing Gum | |
|---|---|
| Ingredients | % |
| Gum base (Natural or Synthetic elastomer filler i.e. gum arabic) | 20-35 |
| Sorbitol | 10-20 |
| Dextranase (5,000-20,000 units/g) | 0.1-1 |
| Sodium Lauryl Sulfate | 0.1-0.5 |
| Betaine | 0.5-1 |
| Crotein Q | 0.5-3 |
| Flavoring | 0.5-2 |
| Dextrose | Q.S. |

The following Table defines additional dextranase-containing dentifrice formulations having physical and cosmetic stability and the retention of enzyme activity upon aging.

Examples 10-18 inclusive comprise an aqueous vehicle containing a suitable flavor material. Examples 10-13 inclusive contain 1.8% dextranase. Example 14 contains 2.1%, Example 15 contains 2.5% and Examples 16-18 inclusive contain 3.6% dextranase. Conventional humectants or mixtures thereof in suitable amounts as defined in this specification, are utilized. Examples 10, 11, 13, 16 and 18 comprise glycerin, whereas Examples 12, 14, 15 and 17 comprise a mixture of glycerin and sorbitol.

EXAMPLES 10-18
Toothpastes

| Ex. | Ingredients | Foam (ml) | Initial Enzyme Activity (units) | Activity After 12 Weeks @ 100° F. | % of Initial |
|---|---|---|---|---|---|
| 10 | Iota*/Alumina, 1.2% SLS, 4% Betaine 2% Crotein Q | 58 | 13,800 | 15,200 | 110 |
| 11 | Iota/Alumina, 3% SLS, 0.9% ALES, 4% Betaine, 2% Crotein Q | 58 | 13,400 | 15,100 | 113 |
| 12 | Silica, 0.3% SLS, 0.9% ALES, 4% Betaine, 2% Crotein Q | 46 | 14,000 | 15,800 | 113 |
| 13 | Iota/Alumina, 1.2% SLS, 5% Betaine, 3% Crotein Q | 71 | 12,500 | 16,100 | 129 |
| 14 | Silica, 1.2% SLS, 4% Betaine, 2% Crotein Q, 1% Amide | 55 | 18,600 | 15,000 | 81 |
| 15 | Silica, 0.6% SLS, 4% Betaine, 2% Crotein Q, 1% Amide | 37 | 23,800 | 18,700 | 79 |
| 16 | Iota/Alumina, 0.3% SLS, 0.9% ALES, 4% Betaine, 2% Crotein Q | 50 | 27,000 | 32,700 | 121 |
| 17 | Silica, 0.3% SLS, 0.9% ALES, 4% Betaine, 2% Crotein Q | 51 | 28,300 | 33,800 | 119 |
| 18 | Iota/Alumina, 1.2% SLS, 5% Betaine, 3% Crotein Q | 60 | 23,200 | 34,300 | 148 |

*Carrageenan

Variations in the above formulations may be made. For example, other anionic surfactants such as higher alkyl benzene sulfonates, fatty acid soaps such as tallow soap, sulfated alcohol ethers and the like may be substituted for the specific anionic surfactants in the examples. Similarly, other betaines and sulfated betaines may be substituted for the specific betaine surfactants in the examples.

Other thickening or gelling agents may be substituted for carboxymethyl cellulose or carrageenan such as starch, Irish moss, gum tragacanth and the like.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

What is claimed is:

1. A foaming, stable oral composition comprising a dextranase in an amount to provide 5,000 to 55,000 units/g of initial enzyme activity a mixed surfactant system consisting of at least one anionic surfactant and an amphoteric surfactant selected from the group consisting of a betaine and a sulfobetaine, in a molar ratio of 1:1 to 1:2 of anionic to amphoteric surfactant, and a cationically modified hydrolyzed collagen protein stabilizer in an effective amount to stabilize said enzyme activity and in the weight ratio of 1:1 to 1:2 anionic surfactant to protein stabilizer, in a dental vehicle, the combination of said amphoteric surfactant and said cationically modified protein stabilizer effective in stabilizing said enzyme activity against loss during aging and against inactivation due to the presence of the anionic surfactant.

2. An oral composition according to claim 1, wherein the said cationically modified stabilizer is a quaternary derivative of hydrolyzed protein.

3. An oral composition according to claim 1, wherein the cationically modified stabilizer constitutes about 1 to 5% by weight of the composition.

4. An oral composition according to claim 1, wherein the dextranase constitutes about 0.5 to 4% by weight of the composition.

5. An oral composition according to claim 1, wherein the anionic surfactant is sodium lauryl sulfate.

6. An oral composition according to claim 1, containing sodium lauryl sulfate and ammonium lauryl ether sulfate.

7. An oral composition according to claim 1, in the form of a toothpaste containing about 30-75% by weight of a water insoluble polishing agent.

8. An oral composition according to claim 1, in the form of a toothpowder containing about 70-80% water insoluble polishing agent.

9. An oral composition according to claim 1, in the form of an aqueous mouthwash containing about 5-10% ethanol.

10. An oral composition according to claim 1, in the form of a chewing gum, comprising about 20-35% of a gum base containing a natural or synthetic elastomer filler.

11. An oral composition according to claim 7, wherein the polishing agent is hydrated alumina.

12. An oral composition according to claim 7, wherein the polishing agent is dicalcium phosphate dihydrate.

13. An oral composition according to claim 7, wherein the polishing agent is silica.

14. A toothpaste according to claim 7, containing a liquid content of 20-75% by weight of the composition.

15. An oral composition according to claim 1, wherein the amphoteric surfactant has the general formula:

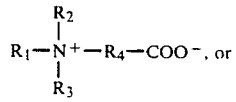

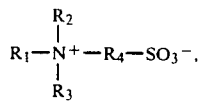

wherein $R_1$ is an alkyl group having 10 to 20 carbon atoms, the amido radical:

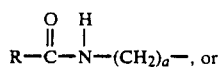, or
the amino radical:
$$R-NH-(CH_2)_a-.$$
wherein R is an alkyl radical of 10 to 20 carbon atoms and a is an integer 1 to 3; $R_2$ and $R_3$ are each alkyl radicals having 1 to 3 carbons; and $R_4$ is an alkylene or hydroxyalkylene group having 1 to 4 carbon atoms, and constitutes about 2-6% by weight of the composition.
* * * * *